United States Patent [19]

Ozaki et al.

[11] Patent Number: 5,411,945

[45] Date of Patent: May 2, 1995

[54] PULLULAN BINDER AND ITS USES

[75] Inventors: Yoshihide Ozaki; Tatsuo Nomura; Toshio Miyake, all of Okayama, Japan

[73] Assignee: Kabushiki Kaisha Hayashibara Seibutsu Kagaku Kenkyujo, Okayama, Japan

[21] Appl. No.: 57,909

[22] Filed: May 7, 1993

[30] Foreign Application Priority Data

Aug. 29, 1992 [JP] Japan ................... 4-272256

[51] Int. Cl.6 ............ C08B 37/00; A61K 31/70
[52] U.S. Cl. ................... 514/23; 106/205; 127/34; 514/54; 514/777; 536/123.12; 536/127
[58] Field of Search .............. 536/123.12, 127; 514/23, 54, 777; 127/34; 106/205

[56] References Cited

U.S. PATENT DOCUMENTS

| | | | |
|---|---|---|---|
| 3,959,009 | 5/1976 | Kato et al. | 127/34 |
| 4,004,977 | 1/1977 | Kato et al. | 127/34 |
| 4,018,233 | 4/1977 | Miyake | 536/1.11 |
| 4,518,581 | 5/1985 | Miyake et al. | 131/274 |
| 4,547,377 | 10/1985 | Ogawa et al. | 426/268 |
| 4,610,891 | 9/1986 | Miyamoto et al. | 427/3 |
| 4,623,394 | 11/1986 | Nakamura et al. | 106/205 |
| 4,629,725 | 12/1986 | Hiji | 514/54 |
| 4,650,666 | 3/1987 | Izutsu et al. | 514/777 |
| 4,777,065 | 10/1988 | Hirao et al. | 106/205 |
| 5,116,820 | 5/1992 | Hiji | 514/54 |
| 5,143,646 | 9/1992 | Nochumson et al. | 252/315.3 |

FOREIGN PATENT DOCUMENTS

| | | |
|---|---|---|
| 45-18254 | 6/1970 | Japan . |
| 105887 | 8/1975 | Japan . |
| 116692 | 12/1975 | Japan . |
| 172566 | 9/1984 | Japan . |
| 246239 | 11/1986 | Japan . |

OTHER PUBLICATIONS

Nippon Starch Refining Co. Ltd; "Adhesive Manufacture", *Chemical Abstracts;* 102:47669, (1985).

Ono et al.; "Adhesive Compositions"; *Chemical Abstracts,* 106:158299y (1987).

*Primary Examiner*—Ronald W. Griffin
*Attorney, Agent, or Firm*—Browdy and Neimark

[57] ABSTRACT

Disclosed is a novel binder which comprises as a main ingredient pullulan and saccharide(s) wherein the weight ratio of said pullulan to saccharide(s) is in the range of 85:15 to 65:35, based on the weight of the dry solid. The binder has a relatively-low viscosity and exerts a satisfiable properties with only a relatively-small amount without a fear of causing an environmental pollution, and because of these it can be advantageously used as a binder in a variety of fields.

21 Claims, No Drawings

PULLULAN BINDER AND ITS USES

BACKGROUND OF THE INVENTION

1. Field of the invention

The present invention relates to a binder which comprises pullulan and saccharide(s) as a main ingredient, and its uses; more particularly, to a binder having a relatively-high binding capacity and a product formed by incorporating said binder in a material.

2. Description of the Prior Art

Pullulan, a viscous glucan which is obtained by culturing under an aerobic condition a microorganism of the species *Aureobasidium pullulans* in a nutritional culture medium containing saccharides such as mono- and oligo-saccharides, has been prepared in an industrial scale.

Pullulan has properties such as satisfiable water-solubility, edibility, film-forming ability and binding capacity, and because of these it has been used as a base, adhesive and coating agent in food products, cosmetics and pharmaceuticals, as well as in a variety of fields of formed products or moldings such as a granule, tablet, rod, film and sheet.

In order to improve the binding capacity of pullulan, it has been proposed to remove concomitant saccharides as much as possible, and this proposal has been actually employed. For example, Japanese Patent Laid-Open Nos.105,887/75 and 116,692/75 disclosed a preparation of a high-purity pullulan by adding an organic solvent to a culture.

The products thus obtained, however, had a relatively-high content of pullulan, it could not be readily used in a variety of industrial fields because the products exhibited a relatively-high viscosity and required a relatively-high production-cost and a skillful handling when dissolved in a solution. Also proposed was a binder containing pullulan which can be readily used in an industrial field. For example, Japanese Patent Laid-Open No.172,566/84 proposed a sizing agent which is obtained by culturing a pullulan-forming microorganism in a culture medium containing torrefaction dextrin as a carbon source.

It was found that the content of pullulan in the composition as disclosed in the Example of the above-mentioned publication was less than 10 w/w % (throughout the specification the symbol "w/w %" is abbreviated as "%", if specified otherwise), based on the weight of the dry solid (d.s.b.), and that the binding capacity of the composition was unfavorably low.

The publication pointed out the drawbacks of torrefaction dextrin, i.e. "torrefaction dextrin was poor in bacterial resistance, and moisture proof and frangibility of a coating film formed therewith, as well as in curling resistance of a paper coated therewith."

According to the Japanese Industrial Standards (JIS), torrefaction dextrin should fulfill the following requirements: It exhibits purplish red on the iodine reaction and contains 6% or lower of glucose as a reducing sugar. The amount of glucose corresponds to about 17 as an average polymerization degree of saccharides.

Japanese Patent Laid-Open No. 246,239/86 proposed a viscous composition wherein a viscosity-imparting substance and a plasticity-imparting substance are mainly incorporated in pullulan, and, if necessary there is further added to the mixture one or more agents such as a filler, coagulation-improving agent and viscosity-controlling agent.

It was found that the composition, however, was insufficient in its binding capacity because it was proposed to incorporate therein 50% or higher saccharides, d.s.b., as a filler, and less than 30% pullulan, d.s.b. Therefore, the invention of the publication has not attained the object.

It has been a great demand to establish a binder which contains pullulan, as well as having a relatively-low viscosity, ready handleability and relatively-high binding capacity without a fear of causing an environmental pollution.

SUMMARY OF THE INVENTION

The present inventors have studied the utilization of saccharides to pullulan in order to establish a binder which contains pullulan, as well as having a relatively-low viscosity, ready handleability and relatively-high binding capacity without a fear of causing an environmental pollution.

As a result, we unexpectedly found that the viscosity of a composition containing pullulan and saccharide(s) in a specific weight ratio was lowered but the binding capacity was more augmented than a product consisting almost entirely of pullulan such as disclosed in the aforementioned JP 105,887/75 and JP 116,692/75, and established a product characterized in that it is formed by incorporating said binder in a material. Thus, we accomplished this invention.

DETAILED DESCRIPTION OF THE INVENTION

The present invention relates to a binder which comprises pullulan and saccharide(s) as a main ingredient, and its uses; more particularly, to a binder having a relatively-high binding capacity and a product formed by incorporating said binder in a material.

We found that a binder which comprises pullulan and saccharide(s) as a main ingredient in a ratio (throughout the specification the wording "ratio" means "weight ratio, d.s.b.") of said pullulan to saccharide(s) being in the range of 85:15 to 65:35 is suitably used in the invention.

The content of the main ingredients suitably used in the invention is a relatively-high level which does not lower the binding capacity of the present binder, preferably, 90% or higher, d.s.b., of pullulan and saccharide(s) in total.

The wording "pullulan" as referred to in the invention means a high-molecular weight substance which is insoluble in 75 v/v % methanol and hydrolyzed by pullulanase (EC 3.2.1.41) to mainly form maltotriose.

In the present invention, pullulans having an average molecular weight of less than about 500,000, preferably, those in the range of about 100,000–300,000, are suitably used because such pullulans have a relatively-low viscosity, readily handleability, and satisfiable binding capacity.

The saccharides usable in the invention are monosaccharides and oligosaccharides having an average polymerization degree of 2–8, preferably, those having an average polymerization degree of 4 or lower. For example, monosaccharides such as xylose, glucose, fructose and galactose; disaccharides such as maltose, sucrose and lactose; oligosaccharides such as maltooligosaccharide, isomalto-oligosaccharide, fructooligosaccharide and galactooligo-saccharide; and other oligosaccharides such as molasses and those from partial hydrolysates of natural polysaccharide resources which have not yet been utilized; can be used in the invention. It is estimated that the coexistence of a specific amount of saccharides in pullulan facilitates the free movement of pullulan molecules and improves the adhesiveness of the mixture to the surface of a substance to be coated, and because of these the binding capacity of the present binder is augmented.

Any method can be suitably used in the invention as long as it can incorporate pullulan and saccharide(s) in a specific ratio, i.e. a ratio of pullulan to saccharide(s) in the range of 85:15 to 65:35. For example, tile present binder is prepared by a method comprising providing an about 3-50% aqueous pullulan solution, and dissolving in the solution a prescribed amount of saccharide(s) selected from the above-mentioned saccharides. If necessary, the product can be spray-dried or dried with a drum dryer and pulverized into a powder.

The present binder can be also prepared by a culture method which can prepare the products having the specific ratio as mentioned above. Any strain of microorganism or its mutant can be used in such a culture method as long as it has an ability to form pullulan.

The carbon sources usable in the culture medium according to the present invention are monosaccharides such as xylose, glucose, fructose, isomerized sugar and transferred saccharide, and other substances such as maltose, sucrose, maltooligosaccharide, isomaltooligosaccharide, molasses and partial starch hydrolysates.

In the culture method, the culture is ceased when the ratio of pullulan to saccharides in the culture medium reaches to a specific ratio while measuring the amounts of the pullulan and saccharides at a prescribed time-interval, and the cells in the culture medium are removed in an usual manner. The solution thus obtained is decolored by the addition of an activated charcoal when a relatively-large amount of pigments is present, and concentrated to obtain the present product. If necessary, the product can be advantageously dried into a powdery product.

If necessary, organic- or inorganic-materials as a supplemental agent such as a color-imparting agent, flavor-imparting agent, antiseptic, antibacterial agent, stabilizer and filler can be advantageously added to pullulan and saccharide(s) in an adequate amount, preferably, in an amount less than about 10%, d.s.b.

The present binder has the following properties:
(1) It has a relatively-low viscosity and a satisfiable handleability when dissolved in a solvent, and exerts a satisfiable binding capacity with only a relatively-small amount;
(2) It has a satisfiable binding capacity and imparts a satisfiable disintegrating-ability under a humid condition to a product formed therewith;
(3) It imparts a relatively-strong strength to a product formed therewith, and, unlike starch the binding capacity of the binder is not lowered by retrogradation; and
(4) It has a satisfiable adhesiveness and a binding capacity to inorganic materials.

Thus, the present invention realized a binder which has a satisfiable handleability and exerts a satisfiable property with only a relatively-small amount as compared with conventional binders containing pullulan.

Thus, the present binder can be advantageously used in a preparation of a formed product.

In case of the preparation of a product with the present binder, it can be advantageously incorporated in the product alone or in combination with a polyhydric alcohol such as glycerine, sorbitol, maltitol and lactitol to meet to its final use.

If necessary, such a product can be advantageously formed by incorporating therein the present binder together with one or more other materials such as polysaccharides excluding pullulan, as well as a plasticizer, filler, adjuvant, surface-active agent, stabilizer, fire retardant, mold release, antibacterial agent, coloring agent, flavor-imparting agent, nutritive, tobacco, cigarette, taste-imparting agent, pharmaceutically active substance, and biologically active substance.

The wording "incorporating the present binder in a material" as referred to in the invention means processes which can incorporate the binder in a material before the completion of its processing. For example, conventional methods such as mixing, kneading, dissolving, soaking, applying, dispersing, spraying and injecting are advantageously chosen.

The following experiments will explain the present invention more in detail.

Experiment 1

Influence of the ratio of pullulan to saccharides on property of binder

Experiment 1-(1)

Preparation of binder

A highly-purified pullulan having a molecular weight of about 150,000, which had been prepared by the purification method as disclosed in Japanese Patent Laid-Open No. 105,887/75, and "MALTOSE HHH", a maltose product commercialized by Hayashibara Biochemical Laboratories, Inc., Okayama, Japan, were dissolved in water in the ratios as shown in Table 1, and the resultant solutions were dried in vacuo and pulverized to obtain binders in the form of powder.

Experiment 1-(2)

Preparation of product formed with binder

Experiment 1-(2)-(a)

Preparation of mixture powder consisting of binder and aluminum oxide

One g of each binder containing pullulan and saccharides in a specific ratio, prepared by the method in Experiment 1-(1), was dissolved in 60 ml water, and the resultant solution was added with 50 g aluminum oxide, mixed to homogeneity with a homogenizer at 3,500 rpm, transferred to a 500 ml eggplant-shape flask, and subjected to a rotary evaporator to remove water. The resultant massive product was kept at 110° C. for 2 hours, decomposed with a mortar, and transferred to a polyethylene bag with a slide fastener. The bag was kept in a desiccator containing silica gel until it was used as a material powder.

Experiment 1-(2)-(b)

Forming

Ten g of a material powder prepared by the method in Experiment 1-(2)-(a) was placed in a polyethylene bag with a slide fastener, admixed to homogeneity with 6% water, and allowed to stand at an ambient temperature overnight. 1.2 g of the resultant product was placed in a metal mold having a diameter of 12 mm, formed by "Autograph AG-D", a computerized test machine for materials commercialized by Shimadzu Seisakusho, Ltd, Tokyo, Japan, at a pressure speed of 1 mm/min and a forming pressure of 100 MPa for 60 seconds, and dried at 110° C. for 20 hours to obtain a product formed with a binder.

Experiment 1-(3)

Measurement of disruptive strength of product formed with binder

The breaking load of the diametral direction of a product formed with a binder was measured. The maximum load was measured by using "LOAD CELL 5000N", an autograph commercialized by Shimadzu Seisakusho, Ltd, Tokyo, Japan, under the conditions of a test speed of 0.5 mm/min, and the value thus obtained was applied to the following formula to calculate the disruptive strength.

Formula: $\sigma = 2P/\pi Dh$ wherein the symbol "$\sigma$" means the disruptive strength (kgf/cm$^2$); "P", the maximum load (kg/f); "D", the diameter (cm) of a product formed with a binder; and "h", the thickness (cm) of a product formed with a binder.

Experiment 1-(4)

Evaluation

The results were as shown in Table 1.

Experiment 2-(3)

Measurement of disruptive strength of product formed with binder

In accordance with the method in Experiment 1-(3), the disruptive strength of the products were measured.

Experiment 2-(4)

Evaluation

The results were as shown in Table 2.

TABLE 2

| Ratio of binder to aluminum oxide | 0.5:50 | 1:50 | 1.5:50 | 2:50 | 2.5:50 |
|---|---|---|---|---|---|
| Binding capacity (kgf/cm$^2$) | 22.0 | 58.2 | 70.0 | 72.0 | 74.9 |
| Judgement | Control | Present invention | Present invention | Present invention | Present invention |

As evident from the results in Table 2, it was revealed that the binder according to the present invention exerts a relatively-high binding capacity when used 2% or higher, preferably, 3–5% to an inorganic material.

The preparations of the present binder and its uses are described in Examples A and B.

Example A-1

TABLE 1

| Ratio of pullulan to saccharides in binder | 100:0 | 95:5 | 90:10 | 85:15 | 80:20 | 75:25 | 70:30 | 65:35 | 60:40 | 50:50 | 0:100 |
|---|---|---|---|---|---|---|---|---|---|---|---|
| Viscosity (cP) (10%, 30° C.) | 72 | 61 | 51 | 43 | 35 | 28 | 23 | 12 | 10 | 7 | 1 |
| Handleability | Difficult | Difficult | Slightly Difficult | Readily handleable | Readily handleable | Readily handleable | Readily handleable | Readily handleable | Readily handleable | Readily handleable | More readily handleable |
| Binding capacity (kgf/cm$^2$) | 44.0 | 45.6 | 49.7 | 58.4 | 58.2 | 58.3 | 58.2 | 58.1 | 48.9 | 38.7 | 10.1 |
| Judgement | Control | Control | Control | Present invention | Present invention | Present invention | Present invention | Present invention | Control | Control | Control |

As evident from the results in Table 1, it was revealed that the products formed with binders having a ratio of pullulan to saccharides in the range of 85:15 to 65:35 show a relatively-low viscosity and exert a conspicuously-high binding capacity, as well as being readily handleable when dissolved in a solvent.

Experiment 2

Examples of uses of the present binder

Experiment 2-(1)

Preparation of binder

In accordance with the method in Experiment 1-(1), a binder was similarly prepared by mixing pullulan and maltose in the ratio of 80:20.

Experiment 2-(2)

Preparation of product formed with binder

In accordance with the method in Experiments 1-(2)-(a) and 1-(2)-(b), 0.5, 1, 1.5 and 2 g of a binder, prepared by the method in Experiment 2-(1), were respectively dissolved in 60 ml water, and the solutions were admixed with aluminum oxide to obtain products formed with the binders in the same manner.

Thirty parts by weight of "PF-20", a pullulan product commercialized by Hayashibara Shoji Inc., Okayama, Japan, was added with 65 parts by weight of water, and 5 parts by weight of "SUNMALT®", a maltose product commercialized by the same incorporation, and the mixture was dissolved under heating- and stirring-conditions. One kg aliquots of the resultant solution were injected to steel vessels, sterilized by heating, and cooled to obtain a binder in the form of liquid.

The ratio of pullulan to saccharides and the average polymerization degree of the saccharides are respectively about 81:19 and about 2.1. The product has a relatively-low viscosity, satisfiable handleability and relatively-high binding capacity without a fear of causing an environmental pollution, and these render it advantageously useful as a binder in products, particularly, in those of agriculture, forestry, fishery, and livestock farming such as feeds, pet foods, seeds and processed woods; as well as in foods, papers, chemicals, products of paper processing industries, and products of mining and manufacturing industries.

Example A-2

To 30 parts by weight of "PF-20", a pullulan product commercialized by Hayashibara Shoji Inc., Okayama, Japan, was added 61 parts by weight of water, 8 parts by weight of "PANORUP ®", an isomaltooligasaccharide syrup having a moisture content of 25%, commercialized by Hayashibara Shoji Inc., Okayama, Japan, and one part by weight of fructose, and the resultant mixture was processed similarly as in Example A-1 to obtain a binder in the form of liquid.

The ratio of pullulan to saccharides and the average polymerization degree of the saccharides are respectively about 75:25 and about 2.2. Similarly as the product in Example A-1, the product has a relatively-low viscosity, satisfiable handleability and relatively-high binding capacity, and these render it advantageously useful in a mixture of inorganic materials for moldings wherein a free-flowing ability is required.

Example A-3

To 30 parts by weight of "PI-20", a pullulan product commercialized by Hayashibara Shoji, Inc, Okayama, Japan, was added 63 parts by weight of water, and 7 parts by weight of "TETRUP", a high maltotetraose syrup having a moisture content of 28%, commercialized by Hayashibara Shoji Inc., Okayama, Japan, and the resultant mixture was similarly as in Example A-1 processed into a syrupy product which was then dried in vacuo and pulverized to obtain a binder in the form of powder.

The ratio of pullulan to saccharides and the average polymerization degree of the saccharides are respectively about 80:20 and about 3.8. The product can be used in a variety of products as a binder, particularly, suitably used in pharmaceutical solid-preparations and pharmaceutical materials for a living body.

Example A-4

A microorganism of the species *Aureobasidium pullulans* IFO 4464 was used as a pullulan-forming microorganism, and a medium consisting of 8 w/v % "SUN ROSE ®", a partial starch hydrolysate commercialized by Hayashibara Shoji, Inc, Okayama, Japan, 0.2 w/v % $K_2HPO_4$, 0.2 w/v % peptone, 0.2 w/v % NaCl, 0.04 w/v % $MgSO_4.7H_2O$, and 0.001 w/v % $FeSO_4$ was used as a culture medium.

Twenty L of the culture medium was sterilized, adjusted to pH 7.0, and inoculated with a seed culture of the microorganism which had been grown in the same culture medium, and incubated at 27° C. for 2 days. After completion of the incubation, the resultant cells were removed to obtain a supernatant which was then added with an activated charcoal to effect decoloration, concentrated, dried and pulverized to obtain a binder in the form of powder.

The yield and the ratio of pullulan to saccharides of the product were respectively about 1.2 kg and about 70:30. The average molecular weight of the pullulan was about 150,000, and the average polymerization degree of the saccharides was about 1.4. The product has a lower viscosity, more readily handleability, stronger binding capacity, and cheaper production cost than a product consisting of "PF-20", a pullulan product commercialized by Hayashibara Shoji, Okayama, Japan. Thus, the product advantageously used as a binder in a variety of products similarly as in Example A-1.

Example B-1

Coating film

A liquid binder prepared by the method in Example A-1 was prepared into a 1.0% aqueous solution, and a fresh egg within 10 hours after the egg-laying was soaked in the aqueous solution for 30 seconds, and dried at 30° C. for 2 hours to form a film on the eggshell.

The shelf life of the product was compared with that of intact egg as a control while keeping them at an ambient temperature of 15°–25° C. As a result, the shelf life of the product was about 5–10-fold longer than that of the control.

Example B-2

Film

A liquid binder prepared by the method in Example A-2 was prepared into a 15% aqueous solution, and 1% carragheenan and 0.1% sucrose monolaurate were dissolved in the aqueous solution. The resultant solution was poured on a polyester film and conveyed at a speed of 3 m/min to form a film 0.03 mm thick, which was then dried with 90° C. hot-air to obtain the captioned product.

Unlike a film consisting of pullulan, the product is an edible film which does not readily dissolve in an aqueous system but gradually dissolves and disintegrates in the aqueous system.

Accordingly, similarly as a medicinal wafer, the product can be advantageously used as an agent for wrapping an unswallowable powdery medicine, as well as a film for fixing an artificial tooth because the product exhibits a satisfiable viscosity when dissolved and disintegrated.

Example B-3

Paste for binding corrugated cardboard

A liquid binder prepared by the method in Example A-1 was prepared into a 3% aqueous solution, and 100 parts by weight of which was admixed with 10 parts by weight of 10% sodium hydroxide for 20 minutes to obtain a carrier part. One hundred parts by weight of water and 40 parts by weight of corn starch were prepared into a slurry which was then added with one part by weight of borax to obtain a main part. The carrier part was gradually admixed with the main part, and further stirred for 5 minutes to obtain a paste.

The level of the viscosity change of the product was lower than that of conventional starch paste. The product and conventional starch paste were subjected to an experiment wherein a 240 $g/m^2$ B-type liner and a 125 $g/m^2$ semicenter were pasted together. As a result, conventional starch paste showed a tendency to cause troubles over a speed of 120 m/min, while the present product exhibited a satisfiable binding capacity without causing any trouble even at a speed of 160 m/min.

Example B-4

Fiber

A liquid binder prepared by the method in Example A-1 was prepared into a 40% solution, and in which alginic acid was dissolved to give a concentration of 2%, d.s.b. The resultant solution as a material solution for spinning was heated to 60° C., and pressed out in the air of an ambient temperature at a pressure of 3 $kg/cm^2$ from a cylindrical nozzle having a diameter of 0.3 mm and a length of 1 mm to form a strand which was then rolled up with a winder while evaporating water to effect drying.

The product having a satisfiable strength was about 20 $\mu m$ thick. The product can be twisted, knitted and woven, and has a readily water-solubility without a fear of causing toxicity and skin stimulation, and these render it suitably used in a defatted cotton, sanitary napkin, gauze and thread for operation.

When mixed with other fibers, the product can be used for an underwear or other clothing because it has a satisfiable hygroscopicity, non electrification and stainability.

Example B-5

Expanded sheet

One hundred parts by weight of polyvinylchloride was added with 60 parts by weight of dioctyl phthalate as a plasticizer, and the resultant mixture was further added with a 50% aqueous solution of a powdery binder, prepared by the method in Example A-4, in an amount of which gave 30% concentration against the total volume. The mixture was kneaded to homogeneity by a mixer and poured onto an aluminum plate by using an applicator to form a sheet 3 mm thick, which was then heated by an air-heating furnace at 190° C. for 10 minutes to obtain an expanded sheet consisting of uniform cells having a coefficient of expansion of about 5-fold.

The product is suitably used as a sound-insulating material, heat-insulating material, crating material, and shock-absorbing material. The product was disintegrated within one month when allowed to soak in a river, while an expanded sheet which had not been added with the product still remained its original shape even after 12 months.

Example B-6

Tee

A mixture consisting of 10 parts by weight of a powdery binder, prepared by the method in Example A-4, and 4 parts by weight of Japanese acid clay (Kambara earth) was sprayed with water to give a moisture content of about 30% under stirring conditions, and the resultant mixture was formed at 120° C. into a tee by an injection molding machine, soaked in a solution of shellac and alcohol, and air-dried to obtain the captioned product.

The product is broken into small masses at a shot, gradually disintegrated by rainwater, and biodegraded. Thus, the product does not spoil the view of a golf course and disrupt the environment.

Example B-7

Flowerpot

A mixture consisting of 100 parts by weight of a powdery binder, prepared by the method in Example A-4, and 15 parts by weight of glycerine was formed at 135° C. into a flowerpot by an injection molding machine, soaked in a dissolved wax, and cooled at an ambient temperature to obtain the captioned product.

The product is gradually disintegrable and biodegradable, and these render it advantageously useful as a flowerpot for transplantation. Plants grown in the product can be planted out without removing it so as not to be damaged.

Example B-8

Fertilizer in the form of rod

Seventy parts by weight of a compound fertilizer comprising 14% N, 8% $P_2O_5$ and 12% $K_2O$, 10 parts by weight of a powdery binder prepared by the method in Example A-4, 15 parts by weight of calcium sulfate, and 5 parts by weight of water were mixed to homogeneity, and the resultant mixture was heated to 80° C. by an extruder, having a L/D ratio of 20, pressure ratio of 1.8 and die diameter of 30 mm, to obtain the captioned product.

In use the product does not require a vessel, and it has a readily handleability and satisfiable strength for a total layer application. The elution speed of the ingredients contained in the product is controllable by changing their compounding ratio. If necessary, the product can be readily added with a plant hormone, agricultural chemical, and soil conditioner.

Example B-9

Formed tobacco product

To 50 parts by weight of a powdered tobacco material prepared from a bright-yellow tobacco plant was added 200 parts by weight of a 2% aqueous solution of a powdery binder prepared by the method in Example A-3, and 0.1 part by weight of lactitol, and the resultant mixture was extruded from a slit of 0.2 mm onto an endless stainless-steel belt, and dried by infrared to obtain 65 parts by weight of a tobacco in the form of sheet having a moisture content of 13%.

The product is suitable as a tobacco or filler for cigarettes, and a binder for cigars and cigarillos. The product inhibits the deterioration of ingredients of tobaccos, and has a relatively-high perfume-retaining ability without a fear of causing unsatisfiable smell and taste when smoked, and because of these you can enjoy a satisfiable flavor and taste. The content of nicotine and the burning speed are controllable by changing the compounding ratio of pullulan in the product.

Example B-10

Facial pack

A facial pack was in an usual manner prepared by mixing 0.5 parts by weight of linolenic acid to homogeneity with a mixture consisting of 1.5 parts by weight of squalane, 0.5 parts by weight of polyoxyethylene hydrogenated castor oil, 5.5 parts by weight of L-sodium lactate, 4.0 parts by weight of glycerine, 50.0 parts by weight of a 40% of a liquid binder prepared by the method in Example A-2, 10.0 parts by weight of ethyl alcohol, and 33.0 parts by weight of refined water.

The product is suitable as a skin-whitening agent, and advantageously used in the prevention and treatment of a local and systemic hyperpigmentation such as chloasma, freckle and sunburn.

Example B-11

Capsule

Forty parts by weight of a powdery binder prepared by the method in Example A-3 and 60 parts by weight of gelatin were mixed, and the resultant mixture was added with 80 parts by weight of water, dissolved by heating at about 60° C., and deaerated to obtain a solution for coating which was then used in an usual manner to encapsulate a high vitamin-E content oil to obtain a soft capsule.

Unlike a capsule consisting of gelatin, the product has properties such as a relatively-high gas-barrier ability, readily solubility in an aqueous system, and ability to stabilize vitamin E.

Example B-12

Sugar coated tablet

A 150 mg crude tablet as a core was coated until it gave about 230 mg with a first coating agent consisting of 40 parts by weight of crystalline maltitol, 20 parts by weight of a 10% aqueous solution of a liquid binder prepared by the method in Example a-1, 12 parts by weight of water, 25 parts by weight of talc, and 3 parts by weight of titanium oxide. Thereafter, the resultant product was coated with a second coating agent consisting of 65 parts by weight of the same crystalline maltitol, 10 parts by weight of the same solution of the liquid binder, i.e. a 10% pullulan solution, and 25 parts by weight of water to obtain a sugar coated tablet having a satisfiable gloss and appearance.

The sugar coating steps of the product are readily feasible, and the product thus obtained has a satisfiable shock-tolerance and retains its high quality for a relatively-long period of time.

As evident from above, the binder according to the present invention has a relatively-low viscosity and exerts a satisfiable properties with only a relatively-small amount without a fear of causing an environmental pollution, and because of these it can overcome the drawbacks of conventional binders, i.e. some binders could not sufficiently exert the inherent properties of pullulan because of their relatively-small content of pullulan; and others, even if they have a relatively-high content of pullulan, are costing binders and not readily handleable because of their relatively-high viscosity.

The present invention facilitates a preparation of a product formed with a binder, particularly, a preparation of a product of inorganic materials having a satisfiable hardness and strength, as well as a preparation of molds and a solid preparation for agriculture, forestry, fishery and livestock farming wherein the free-flowing ability of materials used in their injection steps, as well as the disintegrating ability and meltability of the final products, are required. Accordingly, the establishments of the present binder and a product formed therewith widen the applicability of pullulan by a large margin, and they are greatly significant in the industrial field.

While there has been described what is at present considered to be the preferred embodiments of the invention, it will be understood the various modifications may be made therein, and it is intended to cover in the appended claims all such modifications as fall within the true spirits and scope of the invention.

We claim:

1. A binder which comprises pullulan and saccharide(s) as a main ingredient wherein the weight ratio of said pullulan to saccharide(s) is in the range of 85:15 to 65:35, on a dry solid basis, and the total content of said pullulan and saccharide(s) is at least 90 w/w %, on a dry solid basis.

2. The binder of claim 1, wherein the molecular weight of said pullulan is less than 500,000.

3. A binder according to claim 1 wherein said pullulan has a molecular weight of about 100,000–300,000 and said saccharide(s) is selected from the group consisting of monosaccharides and oligosaccharides having an average polymerization degree of 2–8, and mixtures thereof.

4. The binder of claim 1, wherein the average polymerization degree of said saccharide(s) is 4 or lower.

5. The binder of claim 4, wherein said saccharide is a member selected from the group consisting of xylose, glucose, fructose, galactose, maltose, sucrose, lactose, maltooligosaccharide, isomaltooligosaccharide, fructooligosaccharide, galactooligosaccharide, molasses, oligosaccharides from partial hydrolysates of natural polysaccharide resources, and mixtures thereof.

6. The binder of claim 1, which is in the form of solution or power.

7. The binder of claim 1, which is for an inorganic substance.

8. A product which is formed by incorporating in a material a binder comprising pullulan and saccharide(s) as a main ingredient wherein the weight ratio of said pullulan to saccharide(s) is in the range of 85:15 to 65:35, on a dry solid basis, and the total content of said pullulan and saccharide(s) in said binder is at least 90 w/w %, on a dry solid basis.

9. The product of claim 8, wherein said binder is incorporated in said product together with a polyhydric alcohol.

10. The product of claim 9, wherein said polyhydric alcohol is a member selected from the group consisting of glycerine, sorbitol, maltitol and lactitol.

11. The product of claim 8, wherein the molecular weight of said pullulan is less than 500,000.

12. A product according to claim 8 wherein said pullulan has a molecular weight of about 100,000–300,000 and said saccharide(s) is selected from the group consisting of monosaccharides and oligosaccharides having an average polymerization degree of 2–8, and mixtures thereof.

13. The product of claim 8, wherein the average polymerization degree of said saccharide(s) is 4 or lower.

14. The product of claim 13, wherein said saccharide is a member selected from the group consisting of xylose, glucose, fructose, galactose, maltose, sucrose, lactose, maltooligosaccharide, isomaltooligosaccharide, fructooligosaccharide, galactooligosaccharide, molasses, oligosaccharides from partial hydrolysates of natural polysaccharide resources, and mixtures thereof.

15. The product of claim 8, wherein said binder is in the form of solution or power.

16. The product of claim 8, wherein said material is an inorganic substance.

17. A product according to claim 8 wherein said material comprises an inorganic powder and said binder is present in an amount of 3–5% based on the weight of said material.

18. A product according to claim 8 wherein said material is a pharmaceutical solid preparation.

19. A product according to claim 8 in the form of an adhesive paste.

20. A product in accordance with claim 8 in the form of a molded shape.

21. A shaped product in the form of a film or fiber consisting essentially of pullulan and saccharide(s) as a main ingredient wherein the weight ratio of said pullulan to saccharide(s) is in the range of 85:15 to 65:35, on a dry solid basis, and the total content of said pullulan and saccharide(s) is at least 90% on a dry solid basis.

* * * * *